(12) United States Patent
Singh et al.

(10) Patent No.: US 6,428,772 B1
(45) Date of Patent: Aug. 6, 2002

(54) ACNE TREATMENT COMPOSITION WITH COOLING EFFECT

(75) Inventors: Mohinder Singh, Naperville; Michael A. Wojcik, Plainfield, both of IL (US)

(73) Assignee: Blistex Inc., Oak Brook, IL (US)

( * ) Notice: Subject to any disclaimer, the term of this patent is extended or adjusted under 35 U.S.C. 154(b) by 0 days.

(21) Appl. No.: 09/888,765

(22) Filed: Jun. 25, 2001

(51) Int. Cl.[7] .............................. A61L 9/04; A61L 9/14; A61K 7/02; A61K 9/12; A61K 31/19
(52) U.S. Cl. .......................... 424/45; 424/47; 424/401; 514/159; 514/576
(58) Field of Search ........................... 424/45, 401, 47; 514/159, 576

(56) References Cited

U.S. PATENT DOCUMENTS 5,286,720 A * 2/1994 Niedbala et al. ............ 514/164
5,908,619 A * 6/1999 Scholz .................... 424/78.02

* cited by examiner

Primary Examiner—Frederick Krass
Assistant Examiner—Clinton Ostrup
(74) Attorney, Agent, or Firm—Brezina & Ehrlich

(57) ABSTRACT

A composition for topical aerosol application contains, by weight, a) about 20 to 90% of an active mixture in the form of a solution, gel or lotion with salicylic acid or benzoyl peroxide as active ingredient, and optionally, a polymeric thickening agent for a gel or lotion, and b) about 10 to 80% of a propellant system which includes dimethyl ether. The composition has a temperature in the range of 3 to 25° C. when dispensed.

14 Claims, No Drawings

ACNE TREATMENT COMPOSITION WITH COOLING EFFECT

BACKGROUND OF THE INVENTION

1. Field of the Invention

The invention relates to the field of over-the-counter type acne treatment compositions.

2. Description of Related Art

Compositions for treatment of acne vulgaris, white heads, black heads and comedones are well known. Generally, such compositions include a keratolytic agent, such as salicylic acid, which dissolves the intracellular matrix of the treated lesion and causes the lesion to slough off the body as dead tissue.

Salicylic acid has been approved by the U.S. Food and Drug Administration for treatment of acne in concentrations of 0.5 to 2% by weight. Such compositions may be in the form of a gel, lotion, cream or solution to be applied with pads, spray or pump.

Salicylic acid is sparingly soluble in water, 1 gram dissolving in about 460 ml of water at room temperature (about 0.2% by weight), to produce a solution with a pH of 2.4. Salicylic acid has a far greater solubility in alcohol, 1 gram dissolving in about 2.7 ml, so most acne treatment compositions are based on a mixture of alcohol and water. The presence of alcohol permits a far greater solubility of salicylic acid than would be possible with water alone. However, alcohol is associated with burning or stinging in many people, so it would be advantageous to provide a salicylic acid composition with a reduced alcohol concentration, or which is free of alcohol entirely.

Benzoyl peroxide is approved by the U.S. Food and Drug Administration for treatment of acne in concentrations of 2.5 to 10% by weight. Benzoyl peroxide is, however, sparingly soluble in both water and alcohol, and is usually provided in the form of creme-type products where it is in suspension form.

Mild cooling of the skin is known to be effective in reducing the itching which accompanies acne. To achieve a mild cooling sensation, it is known to use alcohol, common in acne treatments, as well as counter-irritants, such as camphor, menthol and menthyl lactate. In a study reported by Bromm et al in Neuroscience Letters 1995 March, 187:3, pp. 157–160, the effects of cooling and menthol on histamine induced itching were investigated. Both cooling and menthol were found to be effective, although menthol does not reduce skin temperature.

Apart from any effectiveness in reducing itching, counter-irritants are known to be irritating to the skin, as is alcohol, so it would be desirable to achieve cooling without such compounds.

U.S. Pat. No. 5,286,720 discloses a topical treatment for skin lesions, especially warts, comprising salicylic acid and dimethyl ether, the dimethyl ether being a product which evaporates very rapidly to produce a temperature of about −25° to about −60 C. and which essentially freezes the skin while the salicylic acid is providing keratolytic action. While such a composition is useful for treating small lesions, it is much too damaging to the skin to be applied over a wide area as a general treatment for acne.

SUMMARY OF THE INVENTION

It is therefore an object of the invention to provide a product for treatment of acne which has a mild cooling effect.

It is another object of the invention to provide a treatment for acne which can be formulated without alcohol and other skin irritants.

It is a still further object of the invention to provide a treatment for acne which can be dispensed in aerosol form.

In order to achieve these and other objects, the invention is directed to a composition for topical application in aerosol form, which comprises salicylic acid or benzoyl peroxide as active ingredient, in a base which comprises dimethyl ether propellant, the active ingredient being contained in an aqueous solution, gel or lotion comprising, in the case of a gel or lotion, a polymeric thickening agent. Preferably, this composition is also alcohol-free.

DETAILED DESCRIPTION OF THE INVENTION

When salicylic acid is the active ingredient of the composition of the invention, it must be adequately solubilized. Salicylic acid is soluble in alcohols, specifically lower alkanols such as methanol, ethanol, propanol and isopropanol. Alcohol is present in most acne treatment compositions but can irritate the skin, so it would be preferable to formulate a composition without alcohol.

Salicylic acid occurs in the form of acicular crystals or crystalline powder with a melting point of 157–159° C. and a strong tendency to discolor in sunlight and in the presence of ferric salts. While salicylic acid is only slightly soluble in water, salicylic acid can be solubilized by mixing with sodium tetraborate (borax), sodium carbonate or sodium bicarbonate. The reaction with these solubilizing agents both eliminates the crystalline nature of the salicylic acid and buffers the resulting solution to any degree desired, so that a product may be prepared which is close to skin pH. Sodium tetraborate is preferred.

Preferably, the salicylic acid and a solubilizing agent are heated to about 45°–50°C. in aqueous mixture until a clear solution is obtained. Best results are achieved by heating with strong agitation. The resulting solution does not recrystallize, even when subjected to several freeze-thaw cycles (−20° to +45° C.), and no color change occurs during such cycles.

The compositions of the invention can contain about 0.1 to 26% by weight salicylic acid, preferably about 0.5 to 20% by weight, and more preferably about 0.5 to 5% by weight. For solubilization, about 0.05 to 28% by weight of one or more solubilizing agents will preferably be used. In order to operate within FDA guidelines for over-the-counter medications, the compositions will contain 0.5 to 2% by weight salicylic acid.

For the purposes of the invention, salicylic acid or benzoyl peroxide is formulated into a mousse-type composition dispensed by aerosol. Preferably, such composition is also substantially alcohol-free. Where salicylic acid is the active ingredient, it is present in the amounts discussed above, and solubilized with sodium tetraborate, sodium carbonate or sodium bicarbonate as discussed above.

When benzoyl peroxide is the active ingredient, it may be present in an amount of 0.05 to 25% by weight, preferably 0.05 to 15% by weight. For over-the-counter use, the FDA requires that it be present in an amount of 2.5 to 10% by weight.

According to the invention, the solubilized salicylic acid or the benzoyl peroxide is formulated with water and a mild detergent, such as sodium cocoamphoacetate, among others, and preferably with a polymeric thickening agent to form a gel.

A preferred thickening agent is a methyl vinyl ether/maleic anhydride copolymer crosslinked with decadiene, sold as Stabileze® by GAF corporation. This material is a powder which is mixed with water and heated, then reacted with a base such as sodium hydroxide or potassium hydroxide to form a gel of the desired thickness.

Other components of the formulation include natural plant extracts, preservatives and fragrances.

The preferred cooling agent-propellant for the compositions of the invention is dimethyl ether (DME), which is available commercially as DYMEL® from E.I. Dupont de Nemours & Co. Dimethyl ether is fully compatible with salicylic acid, benzoyl peroxide, and the other components of the compositions of the invention, and may be formulated in amounts effective for achieving the desired degree of cooling.

Preferably, the compositions of the invention will contain about 50% by weight of a solution, lotion or gel containing the a active ingredient, and about 50% by weight propellant, of which 30–40% by weight of the composition is dimethyl ether and about 10–20% by weight of the composition is isobutane, butane and propane. The use of other propellants is possible, as well. Broadly, the compositions of the invention can contain up to 10% to 99.9% by weight propellant, with up to 75% by weight dimethyl ether. Greater amounts of dimethyl ether tend to produce excessive cooling, causing freezing of the skin. The desired temperature of the product after application is preferably greater than 3° C., and more preferably in the range of 3 to 15° C., although higher temperature, e.g. up to 25° C., may be permissible.

The preferred compositions of the invention dispense from aerosol containers and form a mushroom-like shape at the application site, the compositions spreading easily and completely absorbing in the skin, disappearing quickly without leaving a heavy residue. The product has a good feel and achieves a desirable cooling effect, quickly eliminating itching.

A preferred stock solution for aerosol dispensing contains, by weight, 30% dimethyl ether, 10% isobutane-butane-propane mixture, 2% salicylic acid, 2% sodium cocoamphoacetate, and water to 100%.

EXAMPLES

Example 1

A gel composition is prepared with the following composition:

| Component | % by weight |
| --- | --- |
| salicylic acid | 2.0 |
| Sodium tetraborate | 1.5 |
| citric acid | 0.34 |
| chelating agent | 0.10 |
| natural plant extracts | 10.0 |
| Thickening agent (polymer) | 3.0 |
| Preservative & fragrance | 0.8 |
| Water | QS to 100% |

To prepare the composition, the thickening agent is hydrated with purified water, heated with continuous stirring and neutralized with sodium hydroxide to achieve the desired thickness. Sodium tetraborate, chelating agent and citric acid are added to pH 4.5 to 5.5, and salicylic acid is added with stirring until a clear solution is obtained. Plant extracts, preservative and fragrance are then added, and the solution is cooled to a gel state.

Dimethyl ether and isobutane propellants are added to the salicylic acid gel to produce a composition containing, by weight, 50% gel, about 30–40% dimethyl ether and about 10–20% isobutane blend. The isobutane stabilizes the gel in the system.

Example 2

A lotion composition is prepared with the following composition:

| Component | % by weight |
| --- | --- |
| benzoyl peroxide (anhydrous) | 10.0 |
| natural plant extracts | 8.0 |
| Thickening agent (polymer) | 2.2 |
| Esters (solubilizing agent) | 7.5 |
| Preservative & fragrance | 0.5 |
| Water | QS to 100% |

The thickening agent is hydrated with purified water with heat and continuous mixing, and neutralized with potassium hydroxide to the desired thickness. The benzoyl peroxide is dispersed in the ester without heating and mixed rapidly until a uniform paste is obtained. The remaining ingredients are added to the ester phase to form a homogeneous paste, which is added into the thickening agent/water mixture with slow stirring. The composition is cooled to room temperature to form a lotion.

Dimethyl ether and isobutane are added into the benzoyl peroxide lotion to form a mixture containing, by weight, 50% lotion, 40% dimethyl ether and 10% isobutane.

Example 3

A solution is prepared with the following composition:

| Component | % by weight |
| --- | --- |
| salicylic acid | 2.0 |
| Sodium hydroxide | 0.4 |
| citric acid | 0.3 |
| sodium borate | 1.0 |
| sodium cocoamphoacetate | 2.0 |
| purified water | QS to 100% |

The above components are mixed together and heated to 40–45° C. with fast mixing. The mixture is cooled to room temperature with mixing until a clear solution is obtained.

Dimethyl ether and isobutane are added into the solution to form a mixture containing 50%, by weight, of the clear solution with 40% dimethyl ether and 10% isobutane.

What is claimed is:

1. A composition for topical application by dispensing from a pressurized to a non-pressurized state, said composition comprising, by weight:

about 20 to 90% of an active mixture in the form of a gel, lotion or liquid comprising an active ingredient selected from the group consisting of salicylic acid and benzoyl peroxide, and, optionally, a polymeric thickening agent; and about 10 to 80% of a propellant system comprising dimethyl ether, said composition containing said dimethyl ether in an amount sufficient to result in a composition at a point of dispensing in the non-pressurized state having a temperature in the range of 3 to 25° C.

2. The composition of claim 1, wherein the active mixture is a gel comprising about 0.05 to 26% of salicylic acid.

3. The composition of claim 1, wherein the active mixture contains 0.5 to 2% salicylic acid.

4. The composition of claim 2, which is non-irritating, and additionally comprises at least one solubilizing agent for the salicylic acid in an amount sufficient to fully solubilize the salicylic acid in the absence of an alcohol.

5. The composition of claim 4, wherein the at least one solubilizing agent is selected from the group consisting of sodium tetraborate, sodium carbonate and sodium bicarbonate.

6. The composition of claim 5, wherein the at least one solubilizing agent is present in an amount of 0.05 to 28% by weight.

7. The composition of claim 1, wherein the active mixture is a lotion comprising about 0.05 to 25% benzoyl peroxide.

8. The composition of claim 7, wherein the active mixture contains 2.5 to 10% benzoyl peroxide.

9. The composition of claim 7, wherein the benzoyl peroxide is solubilized with an ester.

10. The composition of claim 1, wherein the active mixture is present in an amount of about 10 to 60%.

11. The composition of claim 10, wherein the propellant system comprises dimethyl ether and at least one additional propellant selected from the group Consisting of isobutane, butane and propane.

12. The composition of claim 11, wherein the propellant system comprises about 80% dimethyl ether.

13. The composition of claim 11, which comprises about 10 to 40% dimethyl ether and about. 10 to 20% of the at least one additional propellant.

14. The composition of claim 11, wherein said composition has a temperature in the range of 3 to 15C at the point of dispensing.

* * * * *